United States Patent [19]

Carrico et al.

[11] Patent Number: 4,806,546
[45] Date of Patent: Feb. 21, 1989

[54] IMMOBILIZATION OF NUCLEIC ACIDS ON DERIVATIZED NYLON SUPPORTS

[75] Inventors: Robert J. Carrico; William L. Patterson, both of Elkhart, Ind.

[73] Assignee: Miles Inc., Elkhart, Ind.

[21] Appl. No.: 781,332

[22] Filed: Sep. 30, 1985

[51] Int. Cl.$^4$ .................... C07H 21/00; C12Q 1/68
[52] U.S. Cl. .......................... 536/27; 435/6; 435/803; 935/78
[58] Field of Search ............... 435/6, 7, 803; 935/78; 436/501; 536/27; 525/54.2; 564/225

[56] References Cited

U.S. PATENT DOCUMENTS

| | | | |
|---|---|---|---|
| 4,115,305 | 9/1978 | Hornby et al. | 525/54.2 X |
| 4,298,685 | 11/1981 | Parikh et al. | 435/188 X |
| 4,512,896 | 4/1985 | Gershoni | 422/70 X |
| 4,563,417 | 1/1986 | Albarella et al. | 436/504 X |
| 4,581,333 | 4/1986 | Kourilsky et al. | 435/188 X |
| 4,652,517 | 3/1987 | Scholl et al. | 435/6 X |

OTHER PUBLICATIONS

Stuart, W. D. et al., *Proc. Natl. Acad. Sci. U.S.A.*, vol. 78, 1981, pp. 3751–3754.
Bolden, A. et al., *J. Virology*, vol. 16, 1975, pp. 1584–1592.
*Chemical Abstracts*, vol. 100, No. 7, issued Feb. 13, 1984, p. 428, #49710d, Edwards, E. A. et al., "Derivatization . . . Protein".
*Chemical Abstracts*, vol. 83, No. 7, issued Aug. 18, 1975, p. 219, #55269, Goldstein, L. et al., "Derivatized Nylon . . . Enzymes".
Hames, B. D. et al., (ed.) *In* Nucleic Acid Hybridization a Practical Approach IRL Press, Oxford, England, 1985, p. 86.
Bio-Rad Bulletin 1110, Bio-Rad Laboratories, 1986, pp. 1–8.

*Primary Examiner*—Charles F. Warren
*Assistant Examiner*—Jeremy M. Jay
*Attorney, Agent, or Firm*—Andrew L. Klawitter

[57] ABSTRACT

Immobilization of nucleic acids, e.g., DNA and RNA, by contact with a solid support comprising nylon having amide groups that have been derivatized to amidine residues. Derivatization of the nylon support can be accomplished by treatment with an alkylating agent such as a trialkyloxonium salt under anhydrous conditions followed by reaction with an amine. The immobilized nucleic acid is particularly useful as an immobilized probe in hybridization assays to detect specific polynucleotide sequences in a test sample.

7 Claims, No Drawings

IMMOBILIZATION OF NUCLEIC ACIDS ON DERIVATIZED NYLON SUPPORTS

BACKGROUND OF THE INVENTION

This invention relates to means of immobilizing nucleic acids such as DNA and RNA on solid supports. Immobilized nucleic acids find particular use as probes for determining the presence of particular polynucleotide sequences by hybridization with complementary single stranded polynucleotides. Nucleic acid hybridization is useful as an analytical method in the fields of human and veterinary medicine, agriculture, and food science, among others. In particular, the method can be used to detect and identify etiological agents such as bacteria and viruses, to screen microbes for antibiotic resistance, and to detect malignant cells.

Hybridization assays commonly involve the immobilization of either the nucleic acids present in the test sample or the probe nucleic acid. Such solid-phase techniques are concluded with the detection of hybrids formed on the immobilized phase between the probe and complementary sample polynucleotides. By far the most commonly used matrix for immobilization of nucleic acids in these methods has been microporous nitrocellulose membranes. More recently, microporous nylon membranes have become popular because they have better mechanical strength than nitrocellulose. Some manufacturers have introduced positive ionic groups such as quaternary ammonium ions into nylon membranes to improve their wetting proprieties. All of the known nitrocellulose and nylon membranes used to immobilize nucleic acids require high salt to adsorb the polynucleotides to their surface and baking at around 80° C. to permanently fix the adsorbed DNA or RNA.

Detection of resulting immobilized hybrids formed on the solid matrix is conveniently accomplished by the addition of a detectable protein reagent that binds specifically to the hybrids. Normally such protein reagent will comprise an antibody or other binding protein that is specific for binding to a ligand moiety on the probe nucleic acid or to the unique configuration of the hybrid itself. Examples of the former are the detection of probe nucleic acids bearing a biotin or a hapten group by binding of avidin or anti-hapten antibody. Examples of the latter are the use of antibodies selective for DNA.RNA, or RNA.RNA duplexes or intercalated or otherwise antigenically modified duplexes. The specifically binding protein reagent is labeled with a detectable component, commonly an enzyme.

The problem with use of enzyme-labeled, or otherwise detectable, protein reagents to determine hybridization on the conventionally known solid matrices is nonspecific adsorption of such reagent. This nonspecific binding limits the sensitivity of the overall assay procedure. Accordingly, there is a need for better solid matrices for immobilizing nucleic acids, matrices which do not require high salt or baking in order to obtain efficient and stable immobilization. Further, such new matrices are needed particularly for use in hybridization assays, and particularly where resulting hybrids are detected with labeled protein reagents. Also, since hybridization procedures typically require several incubation and washing steps, the known microporous membranes are not amenable to rapid processing because they are fragile and difficult to handle. A solid, more rigid support material would overcome these problems.

SUMMARY OF THE INVENTION

It has now been found that nucleic acids can be efficiently and stably immobilized on a solid support or matrix comprised of nylon having amide groups which have been derivatized to amidine residues. Such derivatization is conveniently accomplished by anhydrous activation of the amide groups of nylon by treatment with an alkylating agent such as a trialkyloxonium salt, followed by anhydrous reaction of the alkylated amide groups with an appropriate amine. The precise nature of the interaction between the nucleic acid and the amidine derivatized nylon support is not fully understood, however, it is believed that electrostatic and perhaps other noncovalent forces are principally involved.

The present method of immobilizing nucleic acids is characterized by several advantages. There is no need for the presence of high salt concentrations to attain adsorption of nucleic acids to the modified nylon surface. Further, there is no need to bake the adsorbed nucleic acids in order to obtain a stable immobilization to the solid support. A particular advantage where proteinaceous reagents such as enzyme-labeled conjugates are to be used in the detection of hybrids formed on the support is that the modified nylon surface exhibits a very low nonspecific binding of such reagents, enabling more sensitive detection limits to be achieved.

DESCRIPTION OF THE PREFERRED EMBODIMENTS

The extent of derivatization of amide groups in the nylon support necessary or desired for a particular nucleic acid hybridization will normally be determined through routine experimentation. Thus, reaction conditions can vary widely depending on the particular needs for the immobilized nucleic acid. Using a bead form of the nylon support as an example, in the normal case it is anticipated that anywhere between 100 and 400 nanomoles of the available amide groups exposed on the surface of a 4.8 mm diameter bead become derivatized. This gives 140 to 560 nanomoles of amidine groups per square centimeter assuming the surface to be smooth. Derivatization of between about 200 and 250 nanomoles of exposed amide groups on such a 4.8 mm diameter bead has been found to be particularly useful in immobilizing nucleic acids.

The first step in the derivatization process involves activation of the amide group with an appropriate alkylating agent under anhydrous conditions. Activating agents will serve to -alkylate the amide to form an imidate salt. Upon subsequent reaction with an amine, amidine residues are formed. Useful alkylating agents include dialkyl sulfates, alkyl triflates, alkyldiphenyl sulfonium salts, alkyl perchlorates, and particularly the trialkyloxonium salts such as the lower alkyl salts, preferably trimethyloxonium and triethyloxonium salts. The salt counteranion will generally be selected from hexachloroantimonate, hexafluorophosphate, and tetrafluoroborate, with the last named counterion being preferred.

The amine employed can be selected from primary and secondary aliphatic and aromatic amines. They can have one or multiple primary and/or secondary amine groups. For example, diaminoethane, diaminohexane, spermidine, spermine and polyethyleneimine are useful. The amine should have at least one primary or secondary amine group to react with the activated amide but, in addition, it can contain cationic or potentially cationic groups such as tertiary and quartenary amines and guanido residues. Particularly useful amines are diamines and polyamines. Good results have been obtained with diamines which result in the formation of aminoamidine residues on the nylon support. Such diamines include alkane diamines, particularly α,ω-alkane diamines having between 2 and 12 carbon atoms, such as 1,6-hexane diamine, ethylenediamine, putresceine, and cadoverine. The resulting amidine residues have the formula:

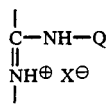

wherein Q is the residue from the amine used to react with the alkylated nylon and X is a counter anion. Where diamines are used, Q will be —R—NH$_2$ where R is preferably alkylene, phenylene, alkyphenylene, or phenalkylene.

A particularly useful general method for derivatizing the nylon support according to the present invention begins with treatment of the support with a solution of trialkyloxonium salt, e.g., trimethyloxonium tetrafluoroborate, in a nonaqueous solvent such as methylene chloride, carbon tetrachloride or diethyl ether. The incubation will proceed for between about 1½ and about 5 hours, preferably with agitation, with about 3 hours being optimal. The temperature of the reaction can vary widely and is primarily a matter of choice. Room temperature treatments are normally used. The activated support is removed from the nonaqueous solution, optionally followed by a series of washings with the nonaqueous solvent. The activated nylon is then reacted with the selected amine, e.g., an alkane diamine such as a 1,6-hexane diamine, in a nonaqueous solvent such as those mentioned above. This reaction is allowed to proceed for about 1 to about 5 hours under ambient conditions, with a reaction time of at least about 3 hours being preferred. Preferably, the derivatized support will then be washed extensively, first with a nonaqueous solvent and finally by water or buffer overnight or longer as desired. The end product can be stored under water or buffer or in dried form.

The nylon support is generally contemplated to comprise any polyamide, including those composed of αω-aminocarboxyl acid monomers as well as those condensed from diamine and dicarbocylic acid monomers. The activation procedure can be applied to any polyamide, regardless of the length of the monomeric units. Aromatic, alkyl, or alkenyl backbones will all give aminocarbalkoxy-substituted nylon. Similarly, the backbone and amide groups can be widely substituted, however, certain functional groups, if present, such as carboxyl, hydroxyl, phenol, and amines, may be modified during alkylation. This can be tolerated so long as the ultimately derivatized nylon serves a substantial function to adsorb nucleic acids.

The conformation and general composition of the support can vary as desired for its application to nucleic acid immobilization provided that there are nylon amide groups exposed at its surface for derivatization and interaction with nucleic acids. The support can be in the form of beads, strips, microtiter wells, test tubes, microporous membranes, and the like. Beads have been found to be particularly advantageous due to their manipulability and high surface area. Particular use has been made of nylon beads having diameters in the range of 1 μM to about 1 cm. Supports comprised uniformly or nonuniformly of nylons can be used, or one can use nylon coated on a non-nylon core or base.

The derivatized nylon support of the present invention can be used to immobilize nucleic acids in general, including DNA, RNA, and derivatives or modifications thereof, comprising any desired number of bases. Genomic and plasmid nucleic acids as well as restriction fragments thereof and synthetic oligonucleotides can be immobilized according to the present invention.

Typically, a desired nucleic acid or population of nucleic acids will be immobilized on the derivatization nylon support by incubation of the support in a buffered solution or dispersion of the nucleic acid. The buffer will preferably be of low ionic strength, normally having a salt concentration of about 0.5M or less and a pH between about 4 and about 10, with about 7 being preferred. Useful buffers include phosphate, carbonate, Tris, and the like, and will contain nuclease inhibitors such as ethylenediamine tetraacetic acid (EDTA), sodium dodecylsulfate, or aurin tricarboxylic acid. The incubation will proceed for between about 1 and 4 hours to obtain saturation of the binding sites. Shorter incubation times can be used where adsorption of less than saturating amounts of the nucleic acid is acceptable. The temperature of the incubation will be preferably between 20° and 60° C., with slightly elevated temperature being preferred, e.g., 50° C. Upon completion of immobilization, the support will then preferably be incubated in a solution of nonspecific nucleic acid, salmon sperm DNA being well known for this purpose, to saturate unoccupied nucleic acid binding sites.

The immobilized nucleic acid can be used in affinity chromatography and purification methods using single- or double-stranded nucleic acids as the affinity ligand, and will find particular application to hybridization assays to detect a particular polynucleotide sequence in a test sample such as biological fluid. In general, the present means for immobilizing nucleic acids can be used in any hybridization protocol involving the use or formation of a solid-phase polynucleotide.

In typical hybridization assays either the sample nucleic acid or a probe nucleic acid is in an immobilized form when brought into contact with the other for purpose of determining complementarity. The probe will have at least one single stranded base sequence substantially complementary to the sequence of interest. The present method for immobilization will in general be more useful for providing immobilized probe to the assay because extended incubation times can be used in manufacturing or preparing this element without increasing the time necessary for the actual assay.

The formation of resulting hybrids, indicating the presence of the sequence of interest in the sample, can be detected in a number of ways. As is known in the art, the one of the sample nucleic acid and the probe which is not immobilized can be labeled with a detectable marker, such as a radioisotope, fluorescer, chemiluminescer, enzyme, or specifically bindable ligand. The amount of such label that becomes associated with the nylon support is thus directly related to the degree of hybridization. Alternatively, dual hybridization methods are known wherein a first portion of the sequence of interest hybridizes with immobilized first probe and is detected by hybridization of a mutually exclusive second portion of the sequence of interest with a labeled or otherwise detectable second probe.

A particularly attractive approach to labeling the probe is to incorporate a binding site for a specific binding substance into the probe molecule either by selection of specific nucleotide sequences or by chemical modification of the probe. Examples of binding sites existing in the nucleotide sequence are where the probe comprises a promoter sequence (e.g., lac-promoter, trp-promoter) which is bindable by a promoter protein (e.g., bacteriophage promoters, RNA polymerase), or comprises an operator sequence (e.g., lac operator) which is bindable by a repressor protein (e.g., lac repressor), or comprises rare, antigenic nucleotides or sequences (e.g., 5-bromo or 5-iododeoxyuridine, Z-DNA) which are bindable by specific antibodies (see British Patent Specification No. 2,125,964). Binding sites introduced by chemical modification of the probe are particularly useful and normally involve linking one member of a specific binding pair to the probe nucleic acid. Useful binding pairs from which to choose include biotin/avidin, haptens and antigens/antibodies, carbohydrates/lectins, enzymes/inhibitors, and the like. Where the binding pair consists of a proteinaceous member and a nonproteinaceous member, it will be preferred to link the nonproteinaceous member to the probe since the proteinaceous member may be unstable under the denaturing conditions of hybridization of the probe. Preferable systems involve linking the probe with a ligand such as biotin or hapten and employing labeled avidin or anti-hapten antibody, respectively. Preparation of useful ligand-labeled probes is known, for example, see European Patent Publication Nos. 63,879 and 97,373; and PCT Publication No. 83-002,286.

Hybridization formats which are particularly useful with the present invention are those involving the use of an immobilized polynucleotide probe and determination of the resulting hybrids by binding of a labeled or otherwise detectable hybrid binding reagent, usually a specific binding protein such as an antibody selective for the hybrid. Antibodies which have selectivity for particular duplexes compared to single stranded nucleic acids and duplexes of other types include antibodies to DNA.RNA, and RNA RNA, and to a limited extent DNA.DNA, as well as antibodies to intercalated duplexes.

Antibodies specific for DNA.RNA hybrids can be stimulated by immunogens comprising homopolymeric or heteropolymeric polynucleotide duplexes. Among the possible homopolymer duplexes, particularly preferred is poly(rA).poly(dT) (Kitagawa and Stollar, *Mol. Immunol.*, 19, 413 [1982]). However, in general, heteropolymer duplexes will be preferably used and can be prepared in a variety of ways including transcription of $\phi$X174 virion DNA with RNA polymerase (Nakazato, *Biochem.*, 19, 2835 [1980]). The selected DNA.RNA duplexes are adsorbed to a methylated protein, or otherwise linked to a conventional immunogenic carrier material, such as bovine serum albumin, and injected with a desired host animal [see Stollar *Meth. Enzymol.*, 70:70 (1980)].

Antibodies to RNA.RNA duplexes can be raised against double stranded RNAs from viruses such as reovirus or Fiji disease virus which infects sugar cane, among others. Also, homopolymer duplexes such as poly(rI).poly(rC) or poly(rA).poly(rU), among others, can be used for immunization as above.

Monoclonal antibodies selective for DNA.DNA duplexes are reported in European Patent Publication No. 135,139.

Antibodies to intercalated duplexes are raised against an immunogen which normally comprises an ionic complex between a cationic protein or protein derivative (e.g., methylated bovine serum albumin) and an anionic intercalated nucleic acid complex. Alternatively, the intercalated complex can be covalently coupled to a carrier protein.

The anti-hybrid antibodies described above will be normally labeled with a detectable group as described above to enable ready determination of hybrids formed on the support of the present invention. Alternatively, the antibody reagent can be detected based on a native property such as its own antigenicity. A labeled anti-(antibody reagent) or protein A will bind to the primary antibody reagent to enable its detection.

The present invention will now be illustrated, but is not intended to be limited, by the following examples.

EXAMPLE 1

A single stranded DNA probe with a sequence complementary to *E. coli* 23s ribosomal RNA was adsorbed onto aminoamidine derivatized nylon beads. The probe was hybridized with *E. coli* 23s RNA and the hybrid was detected with antibody to DNA.RNA hybrids.

Preparation of Aminoamidine Nylon Beads

Burnished nylon beads (4.8 mm in diameter, available from Precision Plastic Ball, Co., Chicago, IL, USA) were placed in methylene chloride, approximately 20 ml per 100 beads. Trimethyloxonium tetrafluoroborate at 0.3 g per 100 beads was added and the solution vigorously stirred for 30 minutes. The beads were removed and quickly washed with methylene chloride, and shaken for 4 hrs in a fresh solution of 1,6-hexanediamine in methylene chloride at 18 mg/ml, 20 ml per 100 beads. The beads were washed with methylene chloride and then with generous amounts of deionized water overnight. They were dried in vacuo at 40°–50° C.

The beads were assayed for amine groups using the TNBS assay. One bead was shaken at room temperature for 3 hours with 0.85 ml of 0.1M $Na_2B_4O_7$ buffer, pH 9.3 containing 1.17 mM trinitrobenzene sulfonate (TNBS) which reacts with amines on the surface and stains the bead yellow-orange. Then 150 $\mu$L of 30 mM glycine was added to react with excess TNBS for 30 minutes. A 40 $\mu$L aliquot of the reaction mixture was diluted into 0.96 mL of 0.1M sodium phosphate buffer, pH 7.0 containing 1.5 mM sodium sulfite and the absorbance at 414 nm was recorded. The total TNBS employed in these reactions was determined with a control prepared as described above except a bead was not included.

A calibration curve is prepared by reacting various levels of glycine (from 0 to 0.8 mM) with 1.6 mM TNBS in the $Na_2B_4O_7$ buffer for 30 minutes. Then 40 $\mu$L aliquots of these reaction mixtures are diluted into 0.96 ml of the phosphate/sulfite solution and the absorbances are recorded. The difference between the total TNBS measured without a bead and the amount of excess TNBS after reaction with a bead gives the molar quantity of amine groups on the bead. Usually each bead contained between 200 and 250 nmoles amine groups.

Adsorption of DNA on Aminoamidine Beads

Twenty-five beads were added to 3.0 mL of 50 mM sodium phosphate buffer, pH 7.4, containing 1 mM ethylenediaminetetraacetic acid (EDTA) and 50 μg of probe DNA. The mixture was shaken at 50° C. for 8.5 hours and 0.22 ml of alkali treated salmon sperm DNA (5.2 mg/mL) was added and the shaking was continued for 4 hours. The beads were transferred into 5.0 ml of hybridization solution and they were shaken at 55° C. for 11 hours. The beads were rinsed twice with 2 to 3 mL of 1 X SSPE, 0.1% SDS and used for hybridization (1 X SSPE is 10 mM sodium phosphate buffer, pH 7.7, 0.18M NaCl, 1 mM EDTA).

Control beads were prepared as follows. Fifty-two aminoamidine nylon beads were added to 6.0 ml of sodium phosphate buffer, pH 7.4, containing 0.5 ml of alkali treated salmon sperm DNA (5.2 mg/mL). The mixture was shaken at 50° C. for 17 hours and the beads were transferred to 6 mL of hybridization solution and shaken at 55° C. for 6 hours. They were rinsed twice with 1 X SSPE, 0.1% SDS.

Preparation of Monoclonal Antibody to DNA.RNA

Preparation of DNA.RNA hybrid - The hybrid was prepared by transcription of φX174 virion DNA with DNA dependent RNA polymerase from *E. coli*. The procedure was described by Nakazato (1980) *Biochem.* 19:2835.

Preparation of methylated thyroglobulin Bovine thyroglobulin (Sigma Chemical Co., St. Louis, MO, USA), 100 mg, was combined with 10 ml of anhydrous methanol and 400 μL of 2.5M HCl in methanol. The mixture was allowed to react for 5 days on a rotary mixer at room temperature. The precipitate was collected by centrifugation and washed twice with methanol and twice with ethanol. Then it was dried under vacuum overnight.

Immunization of mice—One hundred fifty micrograms of DNA.RNA hybrid in 250 μl of 20 mM Trishydrochloride buffer, pH 7.4, 1 mM EDTA was combined with 150 μg of methylated thyroglobulin in 250 μl water. A precipitate formed and 2.5 ml of the Tris buffer was added. The entire mixture was emulsified with an equal volume of Freunds adjuvant. BALB/c mice were each immunized with 0.5 ml of the suspension. Booster immunizations were given 3 weeks later and at one week intervals thereafter. Blood was taken at two week intervals beginning one week after the first boost.

Antibody titers in the serums were measured by an enzyme labeled immunosorbent assay method. Immulon II (Dynateck, Alexandria, VA, USA) microtiter wells were coated with DNA.RNA by placing 50 μl of a 5 μg/ml solution in each well. The DNA.RNA was in 0.015M sodium citrate buffer, pH 6.8, containing 0.15M NaCl. When the solutions had stood at room temperature for 2 hours, the wells were washed with 0.02M sodium phosphate buffer, pH 7.4, containing 5 mg bovine serum albumin/mL and 0.5% Tween 20 detergent (v/v). Appropriate dilutions of antiserums were added to the wells to allow binding of the antibodies to the immobilized DNA.RNA. Then the bound antibodies were detected with enzyme labeled anti-mouse IgG by well-known procedures. Spleen cells from a mouse with a high serum titer to DNA.RNA but low titer to single stranded DNA were fused with myeloma cells to produce hybridomas (Stuart et al [1981]*Proc. Natl. Acad. Sci. USA*, 78:3751; Galfre and Milstein [1981]*Meth. in Enzymol.*, 73:1;) e.g., the cell line deposited with the American Type Culture Collection, Rockville, MD, USA as ATCC HB 8730.

Cloned hybridomas are grown intraperitoneally in mice to produce adequate quantities of antibody for further work. Antibody was isolated from the ascites fluid by anion-exchange high pressure liquid chromatography.

Hybridization Assay for 23s RNA

Each bead was placed in 150 μL of hybridization solutioncontaining the indicated amount of 23s RNA. They were incubated at 55° C. for 30 minutes in 0.5 ml of this solution and finally rinsed once more.

RNA.DNA hybrids formed on the beads were measured by immunoassay. Each bead was shaken at room temperture for 30 minutes in 50 μL of 0.02M sodium phosphate, pH 7.4, 0.15M NaCl, 0.5% (w/v) bovine serum albumin, 0.5% (v/v) Tween 20, 1 mM EDTA (PBS/BSA/Tween/EDTA) and then 100 μL of this solution containing 0.1 μg antibody to RNA.DNA was added. The shaking was continued for 30 minutes and the beads were rinsed twice (0.5 ml each) with 50 mM sodium phosphate buffer, pH 7.4, 0.5% (v/v) Tween, 0.5% (w/v) BSA, 1.0 mM $MgCl_2$ (phosphate/BSA/Tween/$MgCl_2$) One hundred-fifty microliters of phosphate/BSA/Tween/$MgCl_2$ containing β-galactosidase antimouse IgG (diluted 500-fold, Amersham, Chicago, IL, USA) was added to each bead and shaken for 1 hour. The beads were rinsed with 0.5 mL of the phosphate/BSA/Tween/$MgCl_2$ and washed twice for 5 minutes each with shaking and then rinsed once more.

The amount of β-galactosidase label bound to each bead was measured by adding 0.45 mL of 50 mM sodium phosphate buffer, pH 7.4 containing 5 mM $MgCl_2$ and 0.8 mM 7-β-galactosyl-3-[3-dimethyl-aminopropyl-carboxamide]coumarin (Worah et al [1981] *Clin. Chem.*, 27:673) and incubating the mixture at 25° C. for 30 minutes. Then 1.5 ml of the 50 mM sodium phosphate buffer, pH 7.4, 1 mM $MgCl_2$ was added and the fluorescence was recorded.

A substrate control containing only the substrate and buffer was run to correct the results for background fluorescence. Also, the activity of 20 μL of the β-galactosidase conjugate diluted 20,000-fold was measured for calculation of nonspecific binding to the control beads.

The results were as follows:

| DNA on Bead | 23s RNA added to hybridization (pg/assay) | Net Fluorescence |
| --- | --- | --- |
| Probe DNA | 0 | 1220 |
| " | 16.5 | 1395 |
| " | 50 | 1452 |
| " | 165 | 1750 |
| " | 495 | 2560 |
| Salmon sperm (control) | 0 | 16 |
| 20 μL of β-galactosidase antimouse IgG (1:20,000) | | 76 |

The amount of RNA.DNA hybrid detected increased in proportion to the amount of 23s RNA added to the hybridization mixture.

The nonspecific binding of β-galactosidase antimouse IgG to the control bead was 0.035% of the total enzyme conjugate exposed to the bead.

EXAMPLE 2

A study was made of nonspecific binding of β-galactosidase-streptavidin to aminoamidine beads coated with DNA.

Preparation of β-Galactosidase-Streptavidin Conjugate

Sulfhydryl residues on β-galactosidase were exposed by reduction with dithiothreitol. β-Galactosidase (30,000 units, grade VIII, Sigma Chemical Co.) in 2 mL of 0.1M. N-2-hydroxyethyl-piperazine-N'-2-ethane sulfonate buffer (HEPES), pH 7.0, 0.09M NaCl, was combined with 3.5 μmol of dithiothreitol and allowed to stand at room temperature for 4 hours. The dithiothreitol was removed by chromatography on a 2.5×80 cm column of Sepharose Cl-6B (Pharmacia Fine Chemicals, Piscataway, NJ, USA) in the buffer described above. Fractions containing protein were combined into a pool. The number of moles of sulfhydryl groups per mole of enzyme were measured by the method of Ellman (1959) *Arch. Biochem Biophys.*, 82:70.

Succinimidyl-4-(N-maleimidomethyl) cyclohexane-1-carboxylate (SMCC) (Pierce Chemical Co., Rockford, IL, USA), 5.3 mg, was dissolved in 250 μL of anhydrous N,N-dimethylformamide and a 40 μL aliquot was combined with 3 mL of 0.1M HEPES buffer, pH 7.0, 0.15M NaCl. A 25 μL aliquot o this aqueous solution was added to 825 μL of HEPES/NaCl buffer and 100 μL of 1 mM glutathione (reduced form). When this reaction mixture had stood at room temperature for 15 minutes, the unreacted glutathione was determined by Ellman's method. The results were used to calculate the SMCC concentration.

Streptavidin (obtained from Bethseda Research Laboratories, Gaithersburg, MD, USA) was exchanged into 0.1M HEPES buffer, pH 7.0, 0.15M NaCl by gel exclusion chromatography in Biogel P-6DG (Bio-Rad Laboratories, Richmond, CA, USA). Following exchange, 1.75 ml of 3.7 mg/mL streptavidin was combined with 17.6 μL of 61 mM SMCC and allowed to react for one hour at 30° C. The reaction mixture was chromatographed on a 1×25 cm column of Biogel P-6DG in the HEPES buffer. The fractions corresponding to the first effluent peak with absorbance at 280 nm were pooled and assayed for maleimide content by back titration of glutathione as outlined above.

Since the maleimide was subject to hydrolysis, coupling to β-galactosidase was initiated as soon as possible. Activated streptavidin, 3.9 mg, in 3.3 ml of the HEPES buffer was added to 32 mg of reduced β-galactosidase to give a reaction volume of 9.3 ml. After 4 hours at 25° C. the reaction was quenched by adding 800 μL of 1 mM glutathione and incubated an additional 30 minutes t 25° C. Then the reaction mixture was chromatographed on a 1.5×110 cm column of Biogel A-1.5 m (Bio-Rad Laboratories) and developed with 0.1M HEPES buffer, pH 7.0, 0.15M NaCl. Two milliliter fractions were collected and absorbances at 280 nm were recorded. The first peak was pooled for further study.

Measurements of Nonspecific Binding

Beads prepared essentially by the method described for the control beads in Example 1 above were shaken for 30 minutes in 225 μL of 0.1M Tris-hydrochloride buffer, pH 8.0 containing 0.5% BSA, 0.5% Tween 20 and 1 mM MgCl$_2$. Then 25 μL of the β-galactosidase-streptavidin conjugate diluted 100, 500 or 5000-fold was added to appropriate beads and shaken at room temperature for 1 hour. The beads were washed twice by shaking for 5 minutes with 0.5 ml of the Tris-buffer solution containing 0.5M NaCl.

Enzyme adsorbed nonspecifically to the beads was measured by the fluorescent assay described in Example 1. Also, the enzyme activity of the diluted β-galactosidase-streptavidin conjugate was measured and the nonspecifically bound enzyme was calculated.relative to the total enzyme exposed to the bead. The results were as follows:

| Dilution of β-galactosidase-streptavidin | Nonspecific Binding (%) |
|---|---|
| 1:100 | 0.0049 |
| 1:500 | 0.0039 |
| 1:5000 | 0.0062 |

The nonspecific binding was virtually proportional to the level of β-galactosidase-streptavidin exposed to the beads.

EXAMPLE 3

For comparative purposes, a study was made of nonspecific binding of β-galactosidase conjugates to prior art microporous nylon membranes.

Processing of the Membranes

Pall Biodyne A (available from Pall Corporation, Glen Cove, NY, USA) is a nylon membrane with 1.2 μm pores and appended positive and negative ionic groups. A 15 cm$^2$ piece of the membrane was exposed for 1 hour at room temperature to 2 mL of 14 X SSPE containing 50 μg/ml of alkali treated salmon sperm DNA. Then the membrane was air dried and baked at 80° C. in vacuo for 5 hours. The membrane was incubated at 55° C. for 17 hours in 3 mL of hybridization solution. Then it was incubated for 30 minutes in 5 mL of 1 X SSPE, 0.1% SDS.

Nytran (manufactured by Schleicher and Schuell, Keene, NH, USA) is a modified nylon-66 membrane used as a transfer medium for both DNA and protein. It has appended cationic groups. A sample was prepared for a mock hybridization by wetting in distilled water and then soaking in 6 X SSPE for 30 minutes. The membrane was baked at 65° C. in vacuo for 2 hours and incubated in hybridization solution at 55° C. for 17 hours.

Measurements of Nonspecific Binding of Enzyme Conjugates to Biodyne A and Nytran Membranes The membranes were cut into 0.5 cm squares and each square was shaken at room temperature for 60 minutes with 150 μL of PBS/BSA/Tween/EDTA. Then the membranes were rinsed twice with phosphate/BSA/Tween/MgCl$_2$ (0.5 mL each). They were shaken for 1 hour with 150 μL of phosphate/BSA/Tween/MgCl$_2$ containing the indicated dilutions of β-galactosidase-antimouse IgG or β-galactosidase-streptavidin conjugates. The membranes were rinsed once with 0.5 ml of phosphate/BSA/Tween/MgCl$_2$ containing 0.5M NaCl and then washed twice for 5 minutes each with shaking.

Enzyme bound to the membranes was assayed by incubating them at 25° C. for 30 minutes in 250 μL of 50 mM sodium phosphate buffer, pH 7.4, containing 1 mM MgCl$_2$ and 0.8 mM 7-β-galactosyl-3-[3-dimethyl-aminopropylcarboxamide]coumarin. At the end of the incubation 1.5 ml of 50 mM sodium phosphate buffer, pH 7.4, 1 mM MgCl$_2$ was added and the fluorescence was recorded. The enzyme activities of the diluted β-galactosidase conjugates were also measured and the nonspecific binding to the membranes was calculated relative to the amount of enzyme exposed to the membrane. The results were as follows:

For binding of β-galactosidase-antimouse IgG:

| Membrane | β-Galactosidase conjugate dilution | Nonspecific Binding (%) |
| --- | --- | --- |
| Biodyne A | 1:500 | 1.1 |
| " | 1:2000 | 1.2 |
| " | 1:5000 | 1.1 |
| Nytran | 1:500 | 0.88 |
| " | 1:2000 | 0.61 |
| " | 1:5000 | 1.0 |

For binding of β-galactosidase-streptavidin:

| Membrane | β-Galactosidase conjugate dilution | Nonspecific Binding (%) |
| --- | --- | --- |
| Biodyne A | 1:500 | off scale |
| " | 1:2000 | 1.2 |
| " | 1:5000 | 1.6 |
| Nytran | 1:500 | 0.29 |
| " | 1:2000 | 0.69 |
| " | 1:5000 | 0.76 |

The nonspecific binding increased almost in proportion to the β-galactosidase conjugate concentration.

The present invention has been particularly described and exemplified above. Obviously, many other variations and modifications of the invention may be made without departing from the spirit and scope hereof.

What is claimed is:

1. A method for immobilizing a nucleic acid consisting essentially of the step of contacting the nucleic acid with a solid support consisting essentially of nylon having amide groups which have been derivatized to amidine residues of the formula:

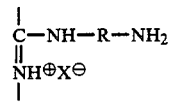

wherein R is alkylene, pheylene, alkyphenylene, or phenalkylene, and X is a counteranion, whereby said nucleic acid becomes bound to the solid support by noncovalent bonds.

2. The method of claim 1 wherein the nylon has been treated to activate the amide groups therein and reacted with an amine to introduce said amidine residues.

3. The method of claim 2 wherein the activation and amine reaction steps are performed under anhydrous conditions.

4. The method of claim 1 whrein the nucleic acid is RNA.

5. The method of claim 2 wherein the amine is an α,ω-alkanediamine having between 2 and 12 carbon atoms.

6. The method of claim 1 wherein the nucleic acid is DNA.

7. The method of claim 1 wherein the solid support is in the shape of a bead.

* * * * *